US009939249B1

(12) United States Patent
Spence

(10) Patent No.: US 9,939,249 B1
(45) Date of Patent: Apr. 10, 2018

(54) BIREFRINGENT CRYSTAL MACH-ZEHNDER INTERFEROMETER

(71) Applicant: Scott E. Spence, Fredericksburg, VA (US)

(72) Inventor: Scott E. Spence, Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/418,956

(22) Filed: Jan. 30, 2017

(51) Int. Cl.
*G01B 9/02* (2006.01)
*G02B 27/10* (2006.01)

(52) U.S. Cl.
CPC .............. *G01B 9/02* (2013.01); *G02B 27/10* (2013.01)

(58) Field of Classification Search
CPC ........................................................ G01B 9/02
See application file for complete search history.

(56) References Cited

U.S. PATENT DOCUMENTS

| 4,671,624 | A | * | 6/1987 | Kahan | G02B 7/028 |
| | | | | | 359/489.04 |
| 5,781,293 | A | * | 7/1998 | Padgett | G01J 3/4531 |
| | | | | | 356/453 |
| 8,149,494 | B1 | | 4/2012 | Spence | 359/288 |
| 8,411,278 | B2 | | 4/2013 | Parks et al. | 356/450 |
| 8,514,478 | B1 | | 8/2013 | Spence | 359/288 |
| 8,619,261 | B2 | | 12/2013 | Parks et al. | 356/450 |
| 8,970,844 | B2 | | 3/2015 | Parks et al. | 356/450 |
| 2002/0159151 | A1 | * | 10/2002 | Li | G02B 6/272 |
| | | | | | 359/484.07 |
| 2012/0268745 | A1 | * | 10/2012 | Kudenov | G01J 3/447 |
| | | | | | 356/453 |

OTHER PUBLICATIONS

S. Spence et al.: "Methods used to observe a dynamical quantum nonlocality effect in a twin Mach-Zehnder interferometer", *Applied Optics* 51 7853 (2012). https://www.osapublishing.org/ao/abstract.cfm?uri=ao-51-32-7853.
S. Spence et al.: "Experimental Evidence for a Dynamical Non-Locality Induced Effect in Quantum Interference Using Weak Values", *Found. Phys.* 42 803 (2012). https://arxiv.org/pdf/1010.3289.pdf (preprint).
J. Tollaksen et al.: "Quantum interference experiments, modular variables and weak measurements", *New J. Phys.* 12 013023 (2010). http://digitalcommons.chapman.edu/cgi/viewcontent.cgi?article=1282&context=scs_articles.
J. Tollaksen et al.: "The Deterministic set of Operators, Quantum Interference Phenomena, and Quantum Reality", *J. Phys. Conf. Ser.* 196 012006 (2009). http://iopscience.iop.org/article/10.1088/1742-6596/196/1/012006/pdf.

* cited by examiner

*Primary Examiner* — Jonathan Hansen
(74) *Attorney, Agent, or Firm* — Gerhard W. Thielman, Esq.

(57) ABSTRACT

A birefringent Mach-Zehnder interferometer (MZI) is provided for optically sensing a small fluctuation from an un-polarized light beam. The birefringent MZI includes first and second birefringent crystals arranged coaxially, the first crystal to receive the beam; and first and second 45° polarizers positioned behind respective the first and second crystals. The first crystal divides the beam into first ordinary and extraordinary rays. The first polarizer converts the first rays into first 45° rays. The second crystal divides the first 45° rays into second ordinary, extraordinary and recombination rays. The second polarizer converts the second rays into second 45° rays.

3 Claims, 5 Drawing Sheets

BIREFRINGENT CRYSTAL MACH-ZEHNDER INTERFEROMETER

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to a Mach-Zehnder Interferometer (MZI). In particular, the invention relates to an MZI using concatenated unseparated crystals.

A Mach-Zehnder Interferometer (MZI) has several optical paths between the input and the output beam-splitters. When one of the optical paths is provided as a reference path, the other optical path can contain an element whose optical path length (product of displacement and index of refraction) can be monitored. Either of the outputs of the MZI is sensitive to optical wavelength phase level fluctuations.

A conventional free-space MZI constitutes a relatively simple device that uses a monochromatic laser, two beam-splitters, two mirrors and screen(s) or camera(s) for detection of the interference profile, interferogram. The conventional MZI configuration typically employs an optical table with regularly tapped holes for holding opto-mechanical mounts that anchor the mirrors and beam-splitters, which are the core components of the MZI. The opto-mechanical mounts typically have micrometer, pivots, and springs in arrangements that are used to finely manipulate the beams of light to cause interference at the output of the MZI. However, the conventional free-space MZI after alignments is neither compact nor stable, due in part to the opto-mechanical mounts.

SUMMARY

Conventional Mach-Zehnder Interferometer (MZI) designs yield disadvantages addressed by various exemplary embodiments of the present invention. In particular, various exemplary embodiments provide a birefringent MZI for optically sensing a small fluctuation from an un-polarized light beam. The birefringent MZI includes first and second birefringent crystals arranged coaxially, said first crystal to receive the beam; and first and second 45° polarizers positioned behind respective the first and second crystals. The first crystal divides the beam into first ordinary and extraordinary rays. The first polarizer converts the first rays into first 45° rays. The second crystal divides the first 45° rays into second ordinary, extraordinary and recombination rays. The second polarizer converts the second rays into second 45° rays.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Various exemplary embodiments provide a free-space, compact, and stable design for a Mach-Zehnder interferometer (MZI) using birefringent crystals. An MZI is employed to observe, detect and/or measure extremely small fluctuations in instrumentation, typically refractive index changes of a signal of interest, such as density changes in fluid flow (gas or liquid), heat transfer, and temperature distribution in plasmas. The exemplary embodiments enable production of a compact and stabilized free-space MZI typically constructed of beam-splitters and mirrors held by opto-mechanical mounts (typically comprised of holders, springs, pivots, and micrometers) subsequently mounted on breadboards or optical tables. A conventional free-space MZI is generally neither very compact nor stable due to its construction.

Compaction of the MZI would render the assembly more readily fieldable, and stabilization enables the instrument to be more easily reproducible as a sensor. In addition, twin and triple sequential MZIs can be implemented with extensions of exemplary embodiments. Both of these sequential MZI configurations have been investigated for future utilities.

Exemplary embodiments utilize a slotted base that aligns, except for rotation, optical elements that are housed in cylindrical devices, in which the cylindrical devices have the same radius on the circular face of the cylinder. The embodiments enable rapid and convenient alignment, which is merely the rotation of the cylindrical devices set in the channel of a slotted base. Further, the exemplary MZI, once aligned, is compact and stable. Exemplary embodiments incorporate birefringent crystals and other polarization types of optics to form the core components of the MZI. The laser can be mounted in a cylindrical device and set in the slotted base for further compactness and stability.

A birefringent crystal possesses two indices of refraction that depend on the polarization of light propagating within the crystal. This crystal need not obey Snell's law, but rather may impose on an extraordinary beam an angular bias for a light ray normal to the incident surface.

Figure 1:
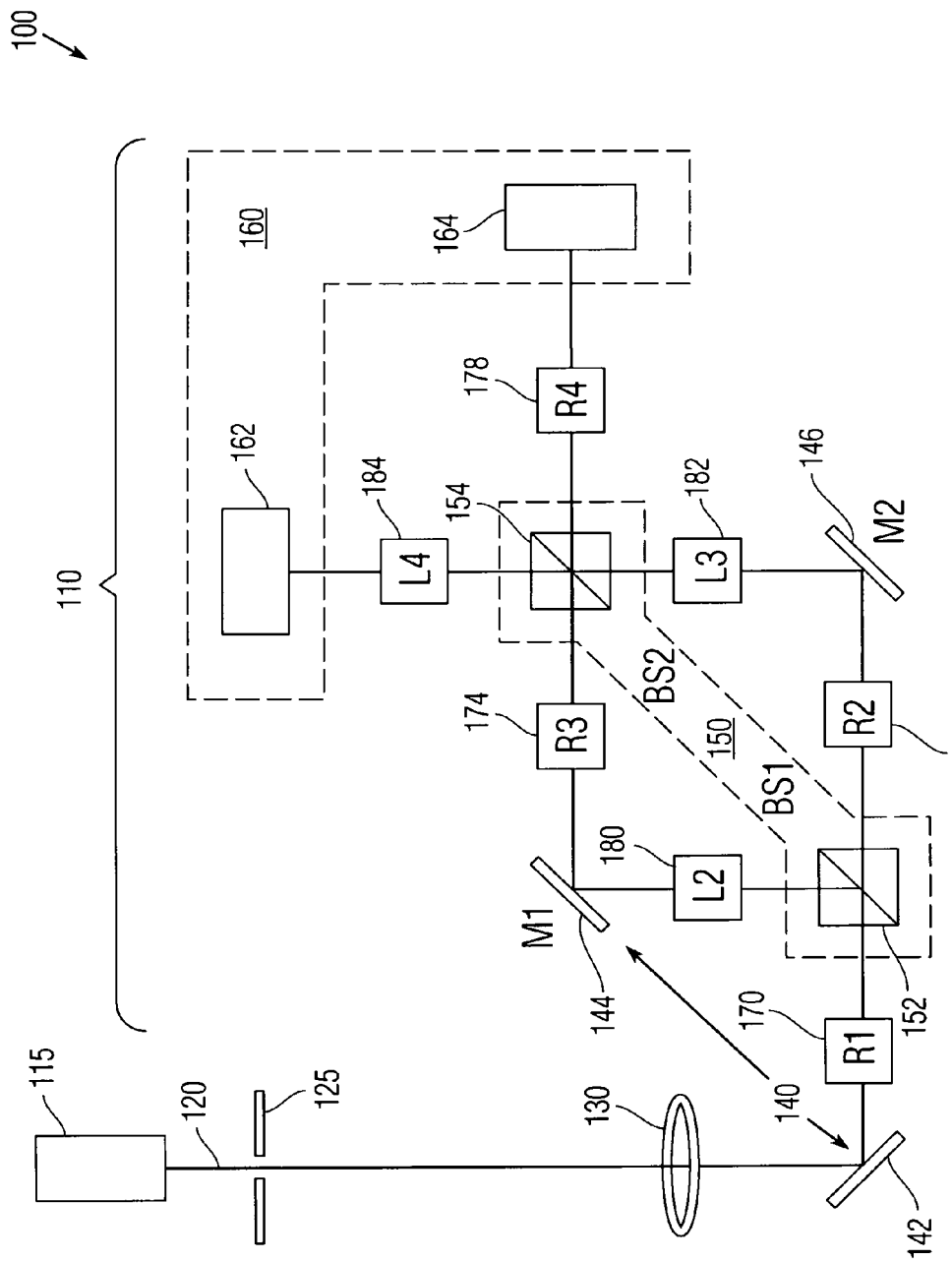
FIG. 1 is a schematic view of a non-polarizing Mach-Zehnder Interferometer (MZI)

FIG. 1 provides a schematic view 100 of a typical non-polarizing MZI 110 compatible with exemplary embodiments. A laser diode 115 emits a beam 120 of photons, which can for example be at wavelength 633 nm. The light beam 120 passes through a spatial filter 125 and a lens 130. A non-polarizing MZI 110 incorporates a plurality of mirrors 140, including first 142, second 144 and third 146 units. The MZI 110 further incorporates a pair of beam-splitters 150 including first 152 and second 154 units. The MZI 110 further incorporates a pair of detectors 160 including first 162 and second 164 units at their respective output ports. The detector 160 can constitute a camera and/or an array of detectors to measure the interference profile of the beam 120.

Following the first mirror 142, the beam 120 engages a plural series of paths, including input first right R1 170, second right R2 172, third right R3 174, fourth right R4 178, first left L2 180, second left L3 182 and third left L4 184. From the input right path R1 170, the first beam-splitter 152 divides the beam 120 into the right path R2 172 and the left path L2 180. From the right path R2 172, the beam 120 reflects via second mirror 146 through the left path L3 182, while from the left path L2 180 the beam 120 reflects via the first mirror M1 144 through the right path R3 174, both paths reaching the second beam-splitter 154. The right path R4 178 leads to the second detector 164, while the left path L4 184 leads the first detector 162.

The output intensities of such an MZI 110 with a phase shift 4, in one of the internal paths has been given from Bachor and Ralph as:

$$I_1(\Delta\varphi) = I_{in}\cos^2\left(\frac{\Delta\varphi}{2}\right), \quad (1)$$

and $$I_2(\Delta\varphi) = I_{in}\sin^2\left(\frac{\Delta\varphi}{2}\right), \quad (2)$$

where phase shift $\Delta\varphi$ applies to the right path R3 174, $I_1(\Delta\varphi)$ is output in right path R4 178, and $I_2(\Delta\varphi)$ is output in left path L4 184. Typically, the ability to measure the phase shift of the wavelength of a light beam 120 is very sensitive.

The MZI 110 in view 100 represents a typical construction using non-polarizing optics, which uses 50/50 beam-splitters 150. However, an alternate MZI can be constructed of polarizing optics, which uses polarizing beam-splitters. Polarization distinguishes photons in the beam 120 by orientation to the plane of incidence to an optical surface. These orientations are labeled P-component for parallel rays and S-component for senkrecht (i.e., perpendicular) rays.

Figure 2:
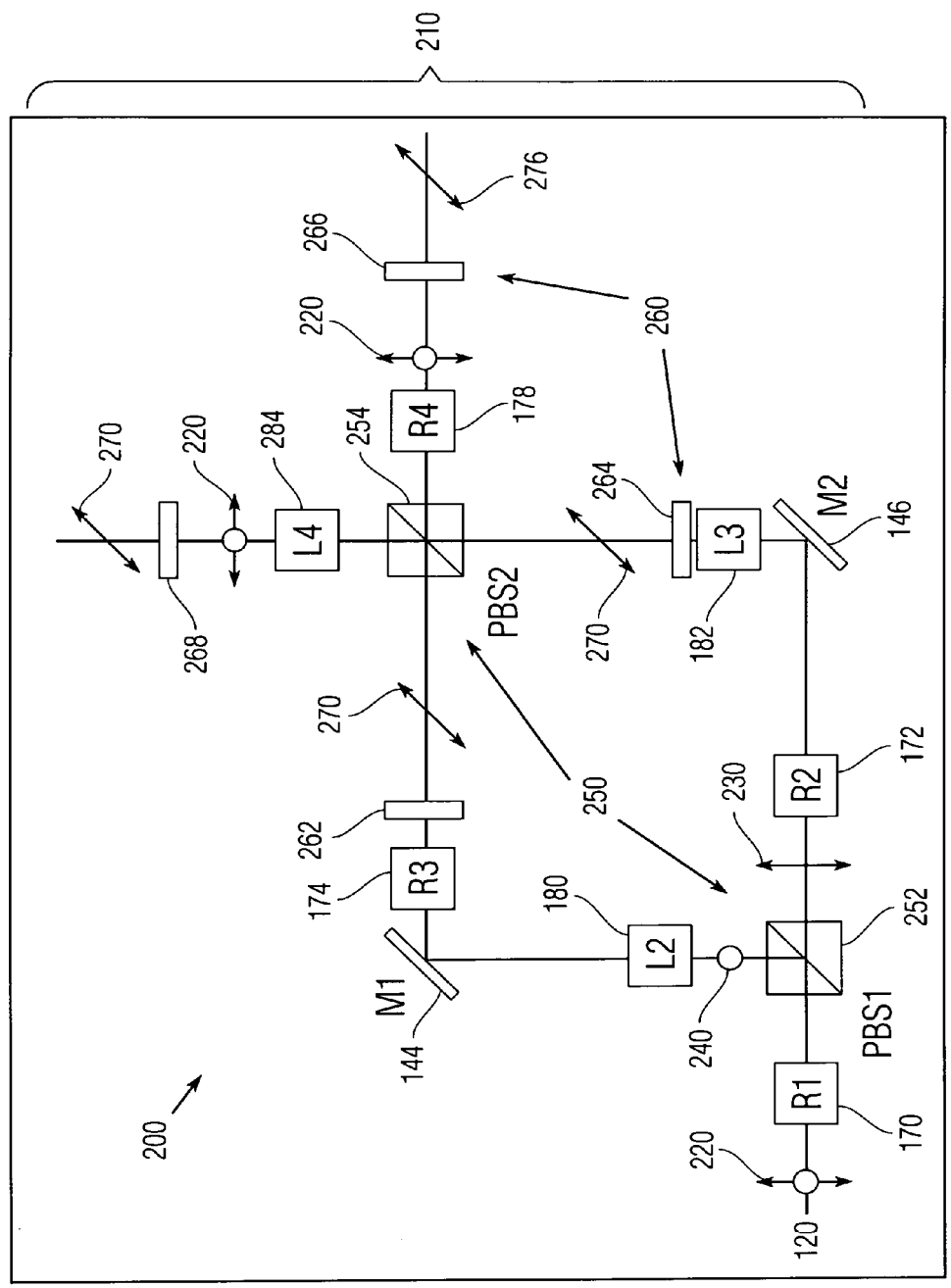
FIG. 2 is a schematic view of a polarizing MZI.

FIG. 2 provides a schematic view 200 of a typical polarizing MZI assembly 210 compatible with exemplary embodiments. This construction is illustrated in view 200 as an intermediate illustration for exemplary embodiments. The polarizing MZI 210 manipulates the beam 120 with its polarization state, characterized by components with respect to the plane of incidence, whether parallel or perpendicular. The beam 120 provides an un-polarized photon ray 220 that comprise a P-component 230 (parallel to the view plane) and an S-component 240 (perpendicular to the view plane).

The polarizations of the beam 120 in the input right path R1 170, as well as of recombined photons 220 along right path R4 178 and left path L4 184, are shown to combine both polarization states. In addition to the plurality of mirrors 140, the MZI 210 incorporates a pair of polarizing beam-splitters 250 that includes first 252 and second 254 units, and a plurality of 45° (i.e., π/4) polarizers 260 that contains first 262, second 264, third 266 and fourth 268 units. The polarizers 260 "erase" the path information of the beam 120 into phase-shifted 45° rays 270.

After passing the input path R1 170, the un-polarized beam 120 enters the first polarizing beam-splitter 252 into a P-component 230 that travels the left path L2 180 and an S-component 240 that travels the right path R2 172. At each of the outputs of the MZI 210 is disposed one of the 45° polarizers 260 to "erase" the path information of the beam 120 into phase-shifted 270 rays, to enable interference. Ideally, both polarization states should incorporate the same amount of power. This can be obtained by rotation of the laser 115 and/or using a waveplate and/or a 45° polarizer 260.

Figure 3A:
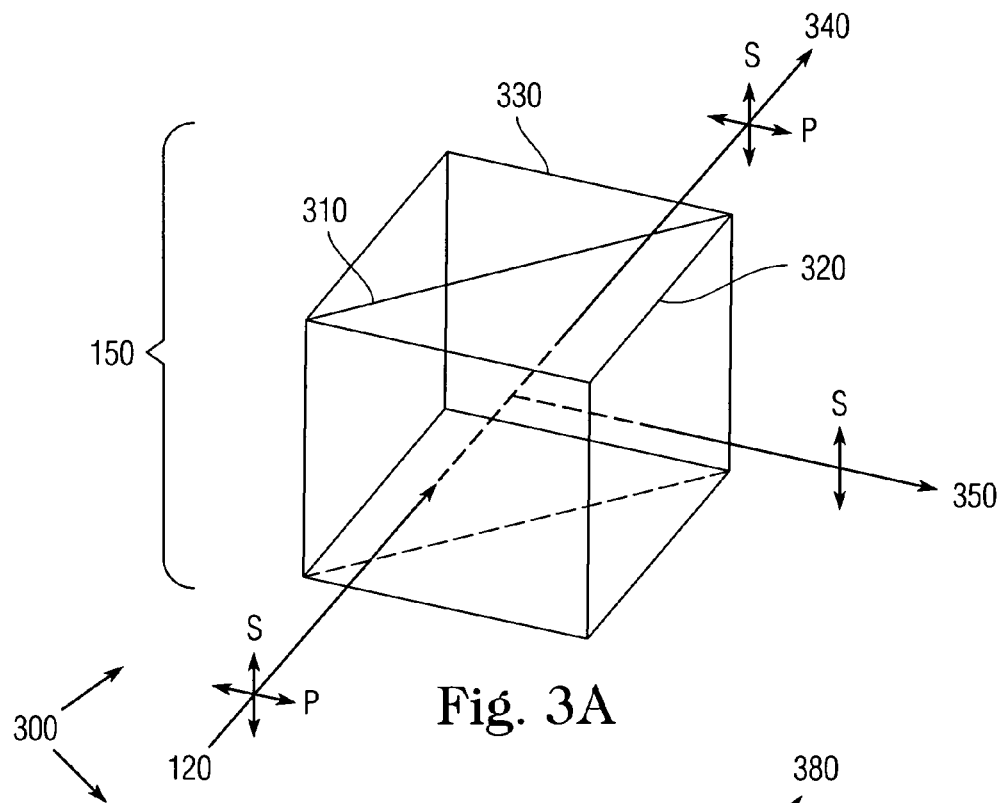
FIGS. 3A and 3B are isometric views of non-polarizing and polarizing beam-splitters.
Figure 3B:
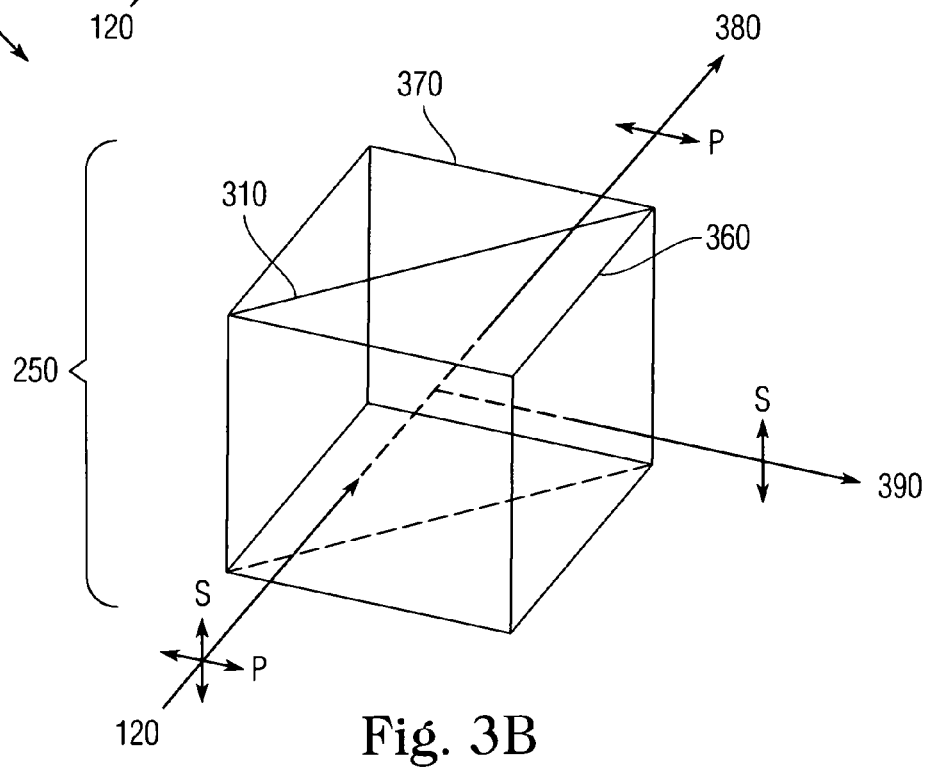

FIGS. 3A and 3B show isometric views 300 of the non-polarizing beam-splitter 150 and the polarizing beam-splitter 250, each having an interface plane 310. The non-polarizing beam-splitter 150 in FIG. 3A includes proximal and distal prisms 320 and 330 joined at the interface plane 310. An incident non-polarized beam 120 enters the proximal prism 320 and splits at the interface plane 310 into a non-polarized transmit beam 340 through the distal prism 330 and an S-polarized reflect beam 350 through the proximal prism 320. The polarizing beam-splitter 250 in FIG. 3B includes proximal and distal prisms 360 and 370 joined at the interface plane 310. The non-polarized beam 120 enters the proximal prism 360 and splits at the interface plane 310 into a P-polarized transmit beam 380 through the distal prism 370 and an S-polarized reflect beam 390 through the proximal prism 360.

A birefringent crystal has properties that resemble the polarizing beam-splitter 250 with the exception that the output light beams exit the crystal offset and parallel with each other. The parallel P-component can be referred to as an extraordinary or e-ray, while the perpendicular S-component can be referred to as an ordinary or o-ray. Snell's law requires no refraction of an incident beam normal to the optical surface of the crystal. The o-ray conforms to Snell's law, whereas the e-ray does not, the differences resulting from the o-ray having an isotropic refractive index and the e-ray having an anisotropic refractive index, which varies between the ordinary and extraordinary refractive indices.

Calcite ($CaCO_3$), also called Iceland spar, constitutes a typical material for birefringent crystals having ordinary and extraordinary refractive indices of 1.658 and 1.486, respectively. Other materials having wide separation between the ordinary and extraordinary respective refractive indices include: sodium nitrate ($NaNO_3$) of 1.5854 and 1.3369, and titanium oxide $TiO_2$ or Rutile) of 2.616 and 2.903.

Figure 4:
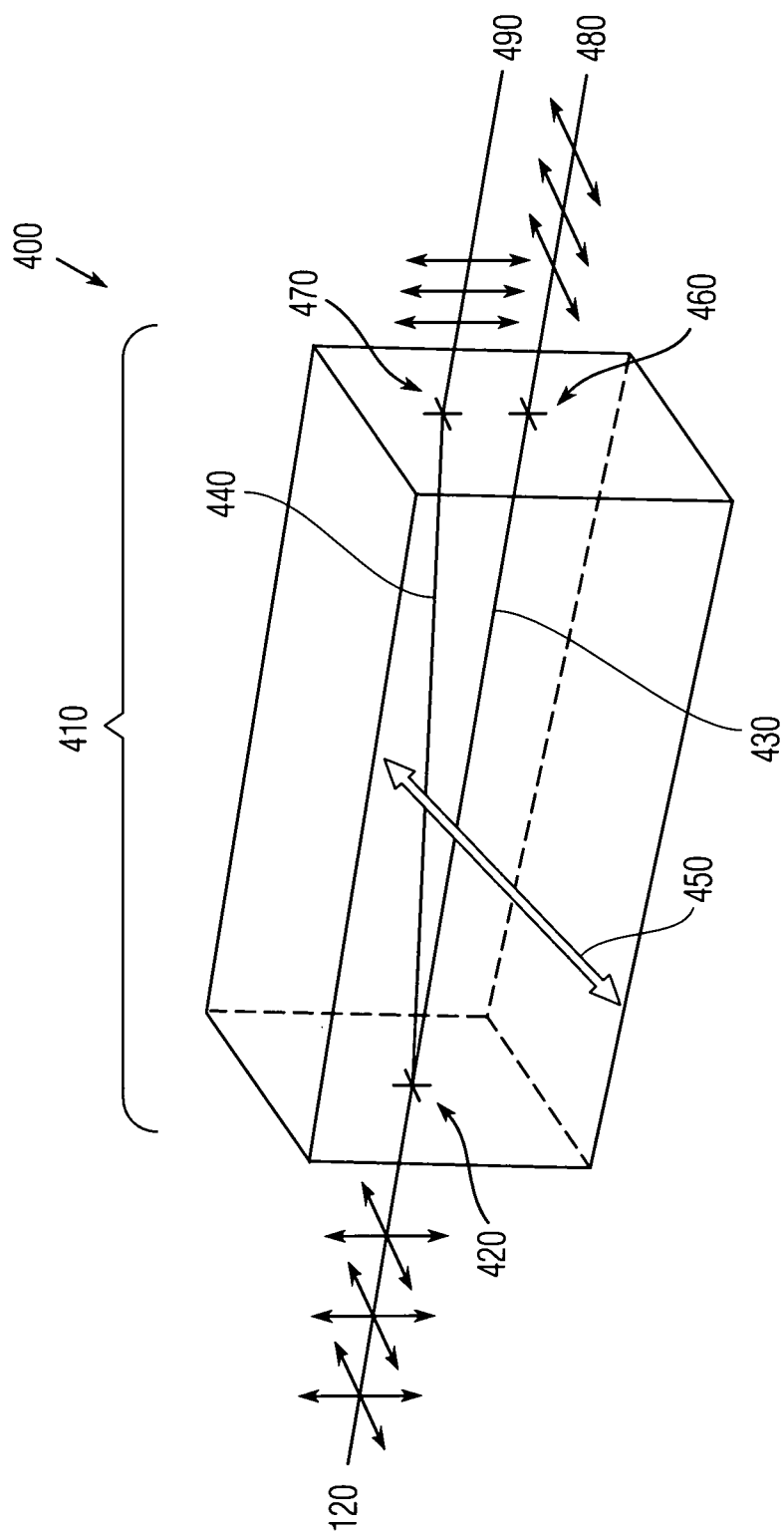
FIG. 4 is an isometric view of a birefringent crystal.

FIG. 4 shows a schematic view 400 of an exemplary birefringent crystal 410. The non-polarized light beam 120 enters the birefringent crystal 410 on an incidence face at an entrance location 420, where the beam 120 splits. The polarization states of the beam 120 diverge to crystal o-ray 430 (in line with the beam 120) and crystal e-ray 440 (acutely tilted from the beam 120), with the divergence characterized by an optical axis 450 orthogonal to the plane of the crystal 410. Both the o-ray 430 and e-ray 440 exit the crystal 410 from an egress face at respective exit locations 460 and 470 as exit o-ray 480 and exit e-ray 490, parallel and offset to each other.

Figure 5:
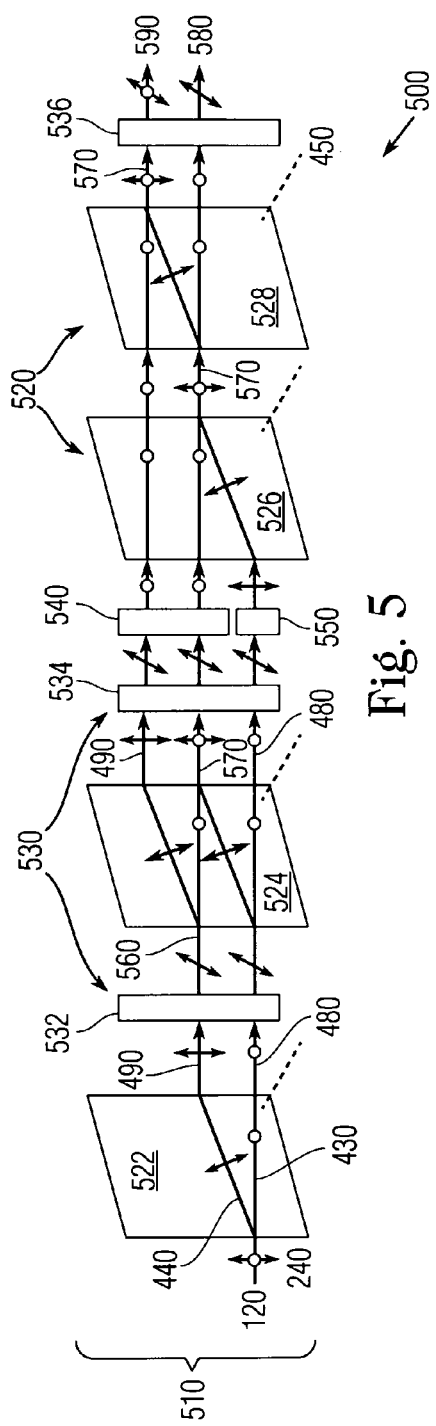
FIG. 5 is a schematic view of concatenated birefringent crystals.

Such birefringent crystals 410 can be concatenated. FIG. 5 shows an optical view 500 of an exemplary birefringent array assembly 510, which includes a coaxial plurality of birefringent crystals 520 analogous to the described example 410. These crystals include first 522, second 524, third 526 and fourth 528 units. The assembly 510 further incorporates a plurality of 45° polarizers 530 that include first 532, second 534 and third 536 units, as well as a horizontal (H) polarizer 540 and a vertical (V) polarizer 550.

The first polarizer 532 is disposed between the first and second crystals 522 and 524. The second polarizer 534 and H/V polarizer 540 and 550 are disposed between the second and third crystals 524 and 526. The third polarizer 536 is disposed behind the fourth crystal 528. The first crystal 522 splits the un-polarized beam 120 into o-ray 480 and e-ray 490. These rays are then erased by the first polarizer 532 to 45° rays 560. These are input to the second crystal 524, splitting each into corresponding o-rays and e-rays, with one e-ray 490 combined with another o-ray 480 into a combined ray 570 with both polarization states.

The second polarizer 534 erases these states along three parallel paths as 45° rays 560, one of which enters the V-polarizer 550 to form an e-ray 490, while the other two enter the H-polarizer 540 to form a pair of o-rays 480. These are received by the third crystal 526, thereby combining the e-ray 490 and one of the o-rays 480, which are input to the fourth crystal 528 that splits the combined ray 570 and combines the remaining o-ray 480, both of which are erased by the third polarizer 536 into a pair of parallel erased rays 560.

Figure 6:
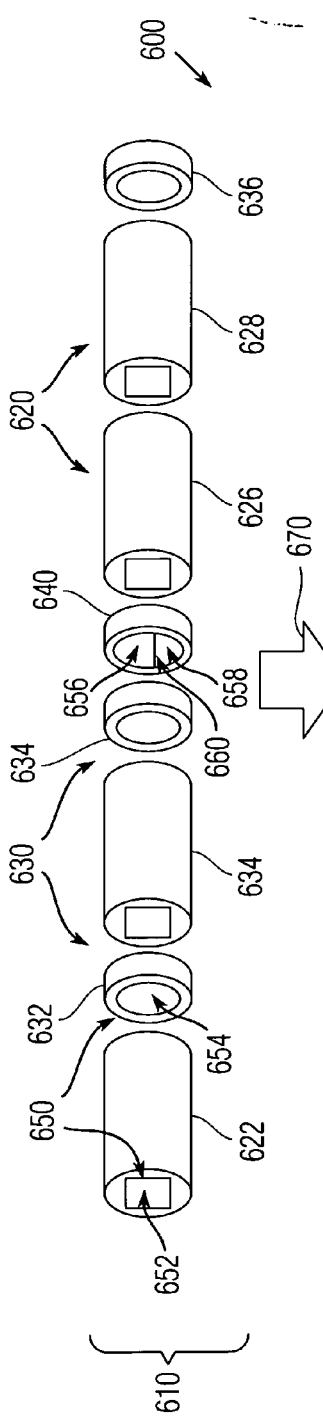
FIG. 6 is an isometric exploded view of an exemplary slotted base architecture MZI.

To illustrate translation into hardware, FIG. 6 shows an exploded isometric opto-mechanical view 600 of an exemplary birefringent MZI assembly 610, which incorporates concatenated tubular components. A plurality of birefringent tubes 620 includes first 622, second 624, third 626 and fourth 628 units, analogous to the crystals 520. A plurality of tubular polarizers 630 includes first 632, second 634 and third 636 units, analogous to the polarizers 630, along with split polarizer 640.

Each of the tubular components features a light channel cross-section 650 for receiving the beam 120 from the laser diode 115. The birefringent tubes 620 have a square cross-section; the polarizers 630 have circular cross-section; the split 640 have upper horizontal 656 and lower vertical 658 chords divided by a waveplate 660. These tubular components can be inserted 670 into an elongated substrate base 680 within a channel slot 690.

The exterior of the tubular components preferably have the same diameter for the purpose of easy alignment that is a property of the opto-mechanical architecture. The relatively soft optical components 522, 532, 524, 534, 540+550, 526, 528, and 536 in annular form, are each bonded inside of their corresponding metal tubular components 622, 632, 624, 634, 640, 626, 628, and 636, respectively. Each of the optical components is properly orientated within their tubular components for proper functioning of the optics. Commercial off-the-shelf parts for the birefringent tubes within a mounted calcite beam displacer for several displaced beams indicate that the tube exterior diameter should be at least one inch (≥1") for a corresponding length of greater than one inch. The diameter and length of birefringent tubes depend on the desired beam separations as well as the birefringent properties of the crystal.

The slotted plate free-space architecture as exemplified in view 600 represented the final design for AT&T's digital optical switching effort in the 1990's by Midwinter. Exemplary embodiments are shown optically in view 500 and opto-mechanically in view 600. A physical embodiment was constructed that showed one input with one interfering output. The laser beam 120 was oriented such that both beams propagated in the first birefringent tube 622.

Instead of a 45° polarizer 634, the waveplate 660 was used to manipulate both of the polarization states that exited the first birefringent tube 622 to obtain the desired mix of two beams that overlapped after exiting second birefringent tube 624. The overlapping beams recombine as un-polarized ray 570 after the second birefringent tube 624. The path information was then "erased" by the second 45° polarizer 634 into 45° rays 560. The optics of this setup was mounted in a cylindrical mount as concatenated tubes as indicated in view 600 and placed in the slotted base 670. The expected interference pattern was readily obtained.

However, FIGS. 5 and 6 show an embodiment of the optics and implementation for a single input dual interfering output quasi MZI device 510. The birefringent crystals 520 have been drawn with the same dimensions were manufactured with the same orientation of the optic axis 450. The length of the crystal (i.e., dimension of the crystal in the same direction as the o-ray) and the orientation of the optic axis 450 determine the separation between the o-ray 480 and e-ray 490, as the rays exit one of the crystals 520.

The proper beam separations between the exits of an upstream crystal with the entrances of its downstream crystal are important to maintain. There were two birefringent crystals depicted as third and fourth birefringent crystals 526 and 528. These two crystals could be replaced by one crystal that is double the length of either birefringent tube. This disclosure should be sufficient for someone who is practiced in this area to easily extend the design to multiple sequential MZI units. Artisans of ordinary skill would also recognize that the birefringent crystal with two indices of refraction for separating a beam into two component polarization states can be replaced with a tri-refringent crystal which has three indices of refraction.

These exemplary embodiments can contribute to improvements in interference sensors and quantum optics. MZIs are key devices in sensing and quantum optics. The exemplary opto-mechanical MZI configuration 610 has desirable key features for such a device, which are a free-space format, compactness, and stability. The main advantage of the exemplary embodiments is enhanced performance via stability. Conventional free-space MZIs are normally constructed of beam-splitters 150 and mirrors 140 held by opto-mechanical mounts. However, integration of a conventional MZI with free-space optical elements cannot be accomplished into a wave-guide integrated circuit format.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A birefringent Mach-Zehnder Interferometer (MZI) for sensing a small light intensity fluctuation from an un-polarized light beam, said MZI comprising:

first and second birefringent crystals disposed coaxially, said first crystal disposed to receive the beam;

first and second 45° polarizers disposed coaxially behind respective said first and second crystals;

a horizontal-and-vertical polarizer disposed coaxially behind said second polarizer;

third and fourth crystals disposed coaxially behind said horizontal-and-vertical polarizer; and a third 45° polarizer disposed coaxially behind said fourth crystal, wherein said first crystal divides the beam into first ordinary and extraordinary rays, said first polarizer converts said first rays into first 45° rays, said second crystal divides said first 45° rays into second ordinary, extraordinary and recombination rays, and said second polarizer converts said second rays into second 45° rays, and said polarizers and crystals produce a pair of phase-shift rays.

2. The birefringent MZI according to claim 1, wherein said crystals are composed of calcite.

3. The birefringent MZI according to claim 1, wherein said crystals and said polarizers are disposed within corresponding metal tubes, such that said crystals provide a square internal cross-section, and said polarizers provide a circular cross-section.

* * * * *